United States Patent
Belongia et al.

(10) Patent No.: US 7,840,123 B2
(45) Date of Patent: Nov. 23, 2010

(54) DIFFUSION DEVICE

(75) Inventors: David C. Belongia, Burlington, WI (US); Mark E. Wefler, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 576 days.

(21) Appl. No.: 11/821,006

(22) Filed: Jun. 21, 2007

(65) Prior Publication Data

US 2008/0315006 A1    Dec. 25, 2008

(51) Int. Cl.
*A61M 16/00* (2006.01)
*H01R 33/00* (2006.01)

(52) U.S. Cl. .................................. 392/392; 362/643
(58) Field of Classification Search ......... 392/359–436; 165/53, 54, 55, 56; 362/643
See application file for complete search history.

(56) References Cited

U.S. PATENT DOCUMENTS

| | | |
|---|---|---|
| 4,568,521 A | 2/1986 | Spector |
| 4,603,030 A | 7/1986 | McCarthy |
| 4,621,768 A | 11/1986 | Lhoste et al. |
| 4,743,999 A | 5/1988 | Hames |
| 4,804,821 A | 2/1989 | Glucksman |
| 4,968,487 A | 11/1990 | Yamamoto et al. |
| 5,038,394 A | 8/1991 | Hasegawa et al. |
| D324,029 S | 2/1992 | Luu |
| RE33,864 E | 3/1992 | Steiner et al. |
| 5,095,647 A | 3/1992 | Zobele et al. |
| 5,114,625 A | 5/1992 | Gibson |
| 5,222,186 A | 6/1993 | Schimanski et al. |
| 5,290,546 A | 3/1994 | Hasegawa et al. |
| 5,402,517 A | 3/1995 | Gillett et al. |
| 5,484,086 A | 1/1996 | Pu |
| 5,554,039 A | 9/1996 | Doudon |
| 5,601,636 A | 2/1997 | Glucksman |
| 5,647,053 A | 7/1997 | Schroeder et al. |

(Continued)

FOREIGN PATENT DOCUMENTS

EP    0962132 A    12/1999

(Continued)

OTHER PUBLICATIONS

International Search Report and Written Opinion in PCT/US2007/020190 dated Jun. 3, 2008.

(Continued)

*Primary Examiner*—Daniel Robinson

(57) ABSTRACT

A diffusion device includes a housing and an opening in the housing adapted for insertion of a container having an active material therein and a wick extending therefrom. The device further includes a heater disposed in a rear portion of the housing and spaced from the wick when a container is inserted into the housing. A vent is disposed in a front portion of the housing. An active material diffusion-interference member is disposed directly above and axially aligned with the wick when the container is inserted into the device, wherein the diffusion-interference member inhibits diffusion of the active material from the housing such that heat generated by the heater is trapped around the wick, thus increasing volatilization and dispersion of the active material from the diffusion device as compared to a diffusion device that does not have a diffusion-interference member.

7 Claims, 17 Drawing Sheets

U.S. PATENT DOCUMENTS

| | | | |
|---|---|---|---|
| D382,658 S | 8/1997 | Yu | |
| 5,662,835 A | 9/1997 | Collingwood | |
| D386,974 S | 12/1997 | Wefler | |
| D393,063 S | 3/1998 | Wefler | |
| D395,494 S | 6/1998 | Becker | |
| D396,275 S | 7/1998 | Pearson | |
| D400,662 S | 11/1998 | Davis | |
| 5,926,614 A | 7/1999 | Steinel | |
| 5,932,147 A | 8/1999 | Chen | |
| 5,957,701 A | 9/1999 | McMillin | |
| 6,013,524 A * | 1/2000 | Friars et al. | 435/420 |
| 6,068,490 A | 5/2000 | Salzberg | |
| 6,104,867 A | 8/2000 | Stathakis et al. | |
| D432,222 S | 10/2000 | Rymer et al. | |
| D433,744 S | 11/2000 | Basaganas | |
| D434,482 S | 11/2000 | Cole | |
| D437,636 S | 2/2001 | Basaganas | |
| D440,291 S | 4/2001 | Wolpert et al. | |
| 6,236,807 B1 | 5/2001 | Ruffolo et al. | |
| D447,550 S | 9/2001 | Basaganas | |
| 6,285,830 B1 | 9/2001 | Basaganas Millan | |
| D449,101 S | 10/2001 | Wolpert et al. | |
| D452,955 S | 1/2002 | Bulsink | |
| D456,886 S | 5/2002 | Hart et al. | |
| D459,459 S | 6/2002 | Yamada et al. | |
| D460,170 S | 7/2002 | Hart et al. | |
| D461,885 S | 8/2002 | Jordi | |
| 6,446,583 B2 | 9/2002 | Vieira | |
| 6,446,880 B1 | 9/2002 | Schram et al. | |
| D465,019 S | 10/2002 | Wu | |
| 6,466,739 B2 | 10/2002 | Ambrosi et al. | |
| D466,204 S | 11/2002 | Wolpert et al. | |
| D469,147 S | 1/2003 | Levine | |
| D473,638 S | 4/2003 | Cruver, IV | |
| 6,567,613 B2 | 5/2003 | Rymer | |
| RE38,150 E | 6/2003 | Greatbatch et al. | |
| D477,065 S | 7/2003 | Lonczak et al. | |
| 6,609,935 B2 | 8/2003 | Huang | |
| D485,334 S | 1/2004 | Fritz | |
| D485,340 S | 1/2004 | Wu | |
| D485,341 S | 1/2004 | Wu | |
| 6,697,571 B2 | 2/2004 | Triplett et al. | |
| 6,714,725 B2 * | 3/2004 | Grone et al. | 392/392 |
| 6,728,478 B2 | 4/2004 | Cox et al. | |
| 6,768,865 B2 | 7/2004 | Stathakis et al. | |
| 6,810,204 B2 * | 10/2004 | Grone et al. | 392/392 |
| 6,832,794 B2 | 12/2004 | He et al. | |
| D501,921 S | 2/2005 | Caserta et al. | |
| 6,850,697 B2 | 2/2005 | Basaganas Millan | |
| 6,853,801 B2 * | 2/2005 | Wefler | 392/392 |
| 6,854,717 B2 | 2/2005 | Millan | |
| 6,862,403 B2 | 3/2005 | Pedrotti et al. | |
| 6,885,811 B2 | 4/2005 | He et al. | |
| 6,889,003 B2 | 5/2005 | Triplett et al. | |
| 6,895,177 B2 | 5/2005 | He et al. | |
| 6,901,215 B2 | 5/2005 | He et al. | |
| 6,917,754 B2 | 7/2005 | Pedrotti et al. | |
| 6,931,202 B2 | 8/2005 | Pedrotti et al. | |
| 6,950,607 B2 | 9/2005 | Yip et al. | |
| D510,423 S | 10/2005 | Caserta et al. | |
| 6,957,012 B2 | 10/2005 | He et al. | |
| 6,966,665 B2 | 11/2005 | Limburg et al. | |
| 7,014,818 B2 | 3/2006 | Rymer | |
| 7,032,831 B2 | 4/2006 | Duston et al. | |
| D521,621 S | 5/2006 | Slater | |
| 7,085,481 B2 | 8/2006 | Hooks et al. | |
| 7,086,607 B2 | 8/2006 | Bresolin et al. | |
| 7,093,949 B2 * | 8/2006 | Hart et al. | 362/96 |
| 7,106,956 B2 | 9/2006 | Caserta et al. | |
| 7,155,116 B2 | 12/2006 | He et al. | |
| 7,164,849 B1 | 1/2007 | Bankers et al. | |
| 7,190,888 B2 | 3/2007 | Wolf et al. | |
| 7,210,812 B1 * | 5/2007 | Linton | 362/183 |
| 7,481,571 B2 * | 1/2009 | Bistritzky et al. | 362/643 |
| 7,542,664 B2 * | 6/2009 | He et al. | 392/390 |
| 7,618,151 B2 * | 11/2009 | Abbondanzio et al. | 362/96 |
| 2003/0063902 A1 | 4/2003 | Pedrotti et al. | |
| 2003/0194355 A1 | 10/2003 | Pedrotti et al. | |
| 2004/0033171 A1 | 2/2004 | Kvietok et al. | |
| 2004/0182949 A1 | 9/2004 | Duston et al. | |
| 2004/0184969 A1 | 9/2004 | Kotary et al. | |
| 2005/0002834 A1 | 1/2005 | Gohil | |
| 2005/0053368 A1 | 3/2005 | Pesu et al. | |
| 2005/0079113 A1 | 4/2005 | Selander | |
| 2005/0180736 A1 | 8/2005 | Zobele | |
| 2005/0195598 A1 | 9/2005 | Dancs et al. | |
| 2005/0196159 A1 | 9/2005 | Zobele | |
| 2005/0213948 A1 | 9/2005 | Caserta et al. | |
| 2005/0218243 A1 | 10/2005 | Zobele et al. | |
| 2006/0016904 A1 | 1/2006 | Caserta et al. | |
| 2006/0120701 A1 | 6/2006 | Caserta et al. | |
| 2006/0163376 A1 | 7/2006 | Lakatos et al. | |
| 2006/0170119 A1 | 8/2006 | Schwarz | |
| 2006/0249593 A1 | 11/2006 | Brown et al. | |
| 2006/0280659 A1 | 12/2006 | Brown et al. | |
| 2007/0036688 A1 | 2/2007 | Hayes-Pankhurst et al. | |
| 2007/0122306 A1 | 5/2007 | Brown et al. | |

FOREIGN PATENT DOCUMENTS

| | | |
|---|---|---|
| EP | 1 103 479 | 5/2001 |
| EP | 1 175 833 | 1/2002 |
| EP | 1 283 062 | 2/2003 |
| WO | WO 97/13539 | 4/1997 |
| WO | WO 98/19526 | 5/1998 |
| WO | WO 98/58692 | 12/1998 |
| WO | WO 03/013618 | 2/2003 |
| WO | WO 03/061716 | 7/2003 |
| WO | WO 03/086487 | 10/2003 |

OTHER PUBLICATIONS

Official Action in U.S. Appl. No. 11/457,728 dated Jun. 30, 2008.
International Search Report and Written Opinion dated Oct. 8, 2008, Appl. No. PCT/US2008/007637.

* cited by examiner

DIFFUSION DEVICE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to diffusion devices that emit active materials, and more particularly to diffusion devices that dispense active materials through a capillary member or a wick.

2. Description of the Background of the Invention

Diffusion devices or diffusers for emitting volatile or active materials are well known in the art. To increase the diffusion of the volatile materials, some diffusion devices include heaters to evaporate and dispense the volatile materials, while others include fans to evaporate and dispense volatile materials. One device having a heater is a plug-in device that includes electrical blades or prongs that are inserted into an electrical socket, wherein the device remains plugged into the socket for extended periods of time. The device includes a housing, a heater disposed within the housing, and a container having a wick extending therefrom and a volatile material disposed therein, wherein the container is adapted to be inserted into the housing such that the wick is disposed adjacent the heater. In order to increase the evaporation of the volatile material from the diffuser, the device further includes an adjustment mechanism that a user must adjust to move the wick toward the heater in order to increase the intensity of heat applied to the wick. In addition, a vent is disposed above or adjacent the wick for immediate dispersion of the volatile material out of the device.

One device that employs a fan includes a housing, a fan disposed within a first side of the housing, and one or more vents disposed in a second side of the housing that is opposite the first side. A container having a wick extending therefrom and a volatile material disposed therein is inserted into the housing such that the wick is disposed between the fan and the vent(s). The fan is cycled on and off to create an airflow through the housing and over the wick to evaporate and dispense the volatile material through the vent(s).

Still other devices utilize both heaters and fans to evaporate and dispense volatile materials into the atmosphere. One of such devices includes a housing, a heater disposed within a rear portion of the housing, and a fan disposed within the rear portion of housing and above the heater. A container having a wick extending therefrom and a volatile material therein is disposed in a front portion of the housing such that the wick is adjacent the heater. A first vent is disposed in the housing directly above the wick to immediately diffuse at least a portion of the volatile material upon vaporization of the volatile material by the heater. The first vent also has a cross-sectional area in a horizontal plane that is, greater than a cross-sectional area in a horizontal plane of the wick. In addition, a plurality of vents is disposed in the front portion of the housing opposite the fan such that any vaporized volatile material that does not exit the first vent is moved through the plurality of vents by the fan. The device also includes an adjustment mechanism that a user must adjust to increase the intensity of the heat applied to the wick. The adjustment mechanism adjusts the intensity of the heat by moving the wick toward and away from the heater.

Therefore, there remains a need for additional ways to increase the rate of diffusion of a volatile material from a diffusion device. A more cost efficient or user friendly device is also desired. The discussion that follows discloses diffusion devices that address one or more of these needs.

SUMMARY OF THE INVENTION

According to one aspect of the present invention, a diffusion device includes a housing and an opening in the housing adapted for insertion of a container having an active material therein and a wick extending therefrom. The device further includes a heater disposed in a rear portion of the housing and spaced from the wick when a container is inserted into the housing. A vent is disposed in a front portion of the housing. An active material diffusion-interference member is disposed directly above and axially aligned with the wick when the container is inserted into the device, wherein the diffusion-interference member inhibits diffusion of the active material from the housing such that heat generated by the heater is trapped around the wick, thus increasing volatilization and dispersion of the active material from the diffusion device as compared to a diffusion device that does not have a diffusion-interference member.

According to another aspect of the present invention, a diffusion device includes a housing and an opening in the housing adapted for insertion of a container having an active material therein and a wick extending therefrom. The device further includes a heater spaced from a portion of the wick when a container is inserted into the housing and a set of vents disposed in a front portion of the housing. A fan is disposed in a rear portion of the housing and spaced from a top portion of the wick, wherein the fan is disposed opposite the vents for moving vaporized active material out of the housing through the vents. An active material diffusion-interference member is disposed directly above and axially aligned with the wick when the container is inserted into the device, wherein the diffusion-interference member inhibits diffusion of the active material from the housing such that heat generated by the heater is trapped around the wick, thus increasing volatilization and dispersion of the active material from the diffusion device as compared to a diffusion device that does not have a diffusion-interference member. Each of the vents has a cross-sectional size and shape in a horizontal plane that is smaller than a cross-sectional size and shape in a horizontal plane of the wick, such that heat generated by the heater is further trapped around the wick.

According to still another aspect of the present invention, a diffusion device includes a housing and an opening in the housing adapted for insertion of a container having an active material therein and a wick extending therefrom. A heater is disposed in a rear portion of the housing and is spaced from the wick when a container is inserted into the housing. A fan is disposed in the rear portion of the housing above the heater and spaced from a top portion of the wick. A set of louvers is disposed adjacent the fan for directing an airflow developed by the fan, wherein the louvers are oriented horizontally when the device is in an operative position. The device includes a set of vents disposed in a front portion of housing opposite the fan and the container is disposed within the front portion of the housing adjacent the rear portion of the housing and opposing projections extend from the rear portion of the housing to limit movement of the container into the housing.

Other aspects and advantages of the present invention will become apparent upon consideration of the following detailed description, wherein similar structures have similar reference numerals.

DETAILED DESCRIPTION OF THE PREFERRED EMBODIMENTS

Figure 1:
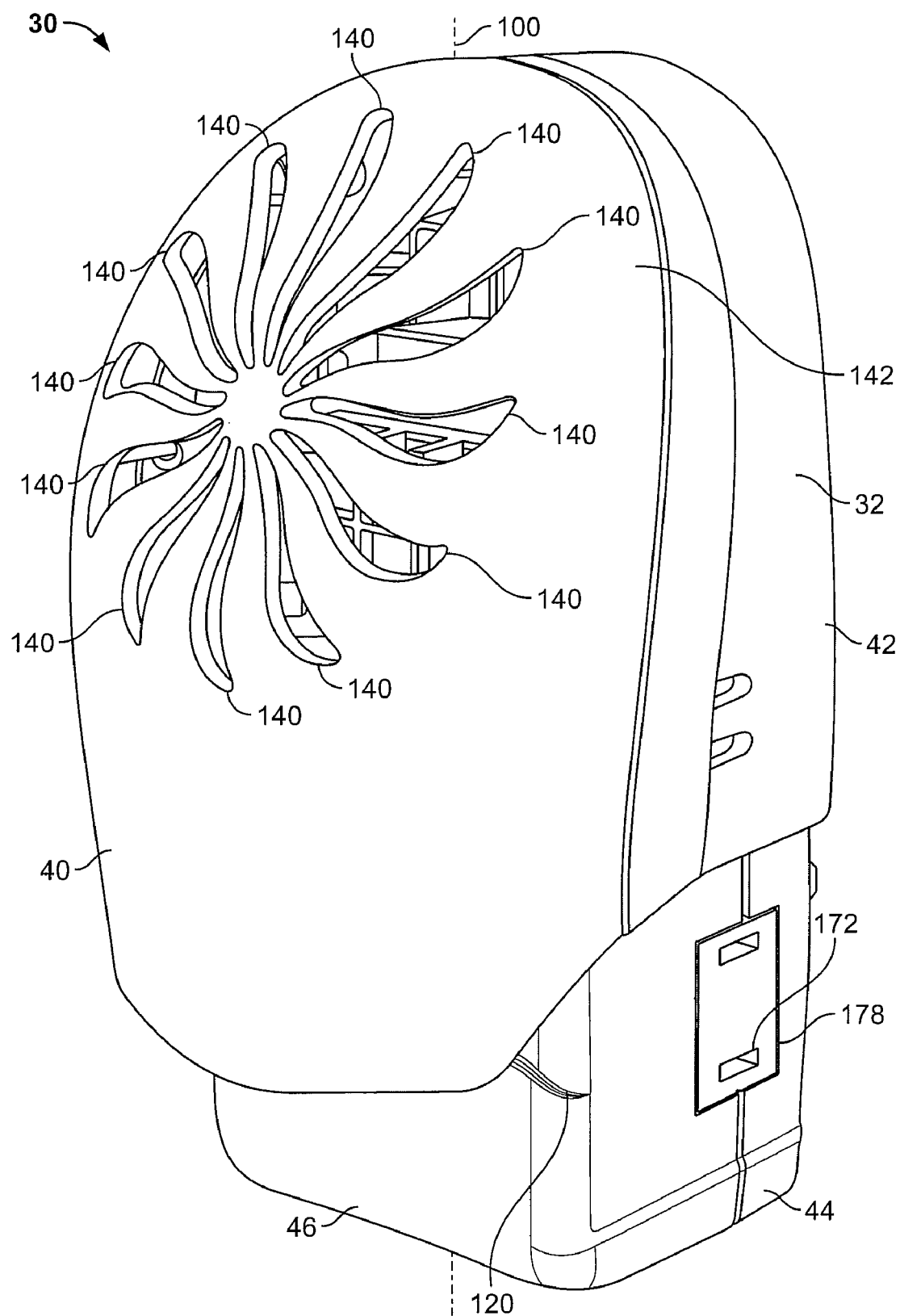
FIG. 1 is a top isometric view of an embodiment of a diffusion device.

It has been discovered that by providing a diffusion device having a heater and/or a fan wherein an active material diffusion-interference member is disposed directly above and axially aligned with a wick that extends from a container into the device (a "non-exposed" wick), the rate of diffusion of an active material from the wick can be increased as compared to a similar device with no active material diffusion-interference member (an "exposed" wick). It has also been found that by providing a diffusion device having a heater and/or a fan wherein an opening disposed above the wick has a cross-sectional size and shape in a horizontal plane that is smaller than a cross-sectional size and shape of the wick in a horizontal plane (a "non-exposed wick), the rate of diffusion of an active material from the wick can also be increased as compared to a similar device with an opening having a cross-sectional size and shape in a horizontal plane that is substantially equivalent to or larger than a cross-sectional size and shape of the wick in a horizontal plane (an "exposed" wick). The horizontal planes as discussed herein refer to planes through the wick and one or more opening when the device is in an operative position. Although not wishing to be bound by theory, and as further explained below, it is believed that by containing heat within the diffusion device by utilizing one or more active material diffusion-interference members and/or not placing an opening having a cross-sectional size and shape in a horizontal plane substantially equivalent to or larger than a cross-sectional size and shape of the wick in a horizontal plane and disposed above the wick, superior diffusion rates can be achieved.

Turning now to the drawings, FIGS. 1-11 illustrate one embodiment of the present invention that includes a diffusion device 30 for emitting active materials therefrom. The device 30 includes a housing 32 in which a container 34 (FIGS. 2 and 12-14) is detachably retained, wherein the container 34 includes a "non-exposed" wick 36 extending therefrom. A "non-exposed" wick occurs when a device 30 in which the container 34 is used includes an active material diffusion-interference member disposed directly above and axially aligned the wick 36 and/or the device 30 does not have an opening or vent disposed above the wick 36 and having a cross-sectional size and shape in a horizontal plane substantially equivalent to or larger than a cross-sectional size and shape of the wick 36 in a horizontal plane. In other words, any opening disposed above the wick 36 has a cross-sectional size and shape in a horizontal plane that is less than a cross-sectional size and shape in a horizontal plane of the wick 36. In a device with a "non-exposed" wick 36, there may be vents, but the vents are configured to retain heat from, for example, a heater, within the device around the wick 36 such that active material in the wick 36 is more quickly vaporized. As illustrated in FIGS. 1-4, vents 140 may be provided to allow diffusion of the active material from the diffusion device, but the area directly above and directly surrounding the top of the wick is mostly enclosed by the housing 32 and the active material diffusion-interference member, as discussed in greater detail hereinafter. By utilizing vents 140, none of which have a cross-sectional size and shape in a horizontal plane substantially equivalent to or larger than a cross-sectional size and shape of the wick 36 in a horizontal plane, and/or by utilizing an active material diffusion-interference member, heat may be trapped around the wick 36, causing the temperature surrounding the wick 36 to increase as compared to a housing that allows the majority of the heat to rise and escape through the top of the housing above or directly surrounding a top of the wick 36.

As used herein, an "exposed" wick is a wick that, when a container having a wick is inserted into a diffusion device, no active material diffusion-interference members are disposed directly above and axially aligned with the wick and a vent having a cross-sectional size and shape in a horizontal plane and that is substantially equivalent to or larger than a cross-sectional size and shape of the wick in a horizontal plane is disposed directly above the wick to disperse an active material that is volatilized by the device directly into the surroundings. An example of an "exposed" wick is shown and described in Pedrotti et al. U.S. Pat. No. 6,862,403. Pedrotti discloses a vaporizer 100 having a bottle 120 with a wick 190 extending therefrom, wherein the bottle 120 is inserted into the vaporizer 100. The vaporizer 100 includes a heater 250 spaced from the wick 190 and an opening 320 disposed immediately above the wick 190 and having a cross-sectional size and shape in a horizontal plane that encompasses and is larger than a cross-sectional size and shape in a horizontal plane of the wick 190 for dispersing volatilized active material. Vents 310 are also disposed in a front portion of the housing opposite a fan unit 260.

The container 34 includes an active material, such as for example, a liquid formulation including a fragrance, a disinfectant, a sanitizer, an air purifier, an aromatherapy scent, an antiseptic, an odor eliminator, an air freshener, a deodorizer, an insecticide, an insect repellant, an insect attractant, or any other active material(s) or ingredient(s) that are usefully dispersed into the air. The term "container" as used herein is used in its broadest sense to include any receptacle that is capable of holding an active material in liquid form.

As best seen in FIGS. 1-4, 10, and 11, the housing 32 includes a front portion 40 and a rear portion 42 connected to the front portion 40. As seen in FIGS. 1, 2, 5-7, 10 and 11, the rear portion 42 includes first and second shell portions 44, 46. An electrical plug assembly 50 is disposed within the first shell 44 and extends outwardly therefrom. The plug assembly 50 may serve the dual purpose of supplying power to electrical components of the device 30 and also supports the device 30 within a wall outlet. The plug assembly 50 includes two plug blades 52 that are inserted into the wall outlet for operation of the device 30. The remaining components of the plug assembly 50 will be discussed in greater detail hereinafter. The plug assembly 50 may be rotatable to allow for rotation of the blades 52. Rotation of the blades 52 allows the device 30 to be utilized in a wall outlet with horizontal or vertical apertures.

Figure 4:
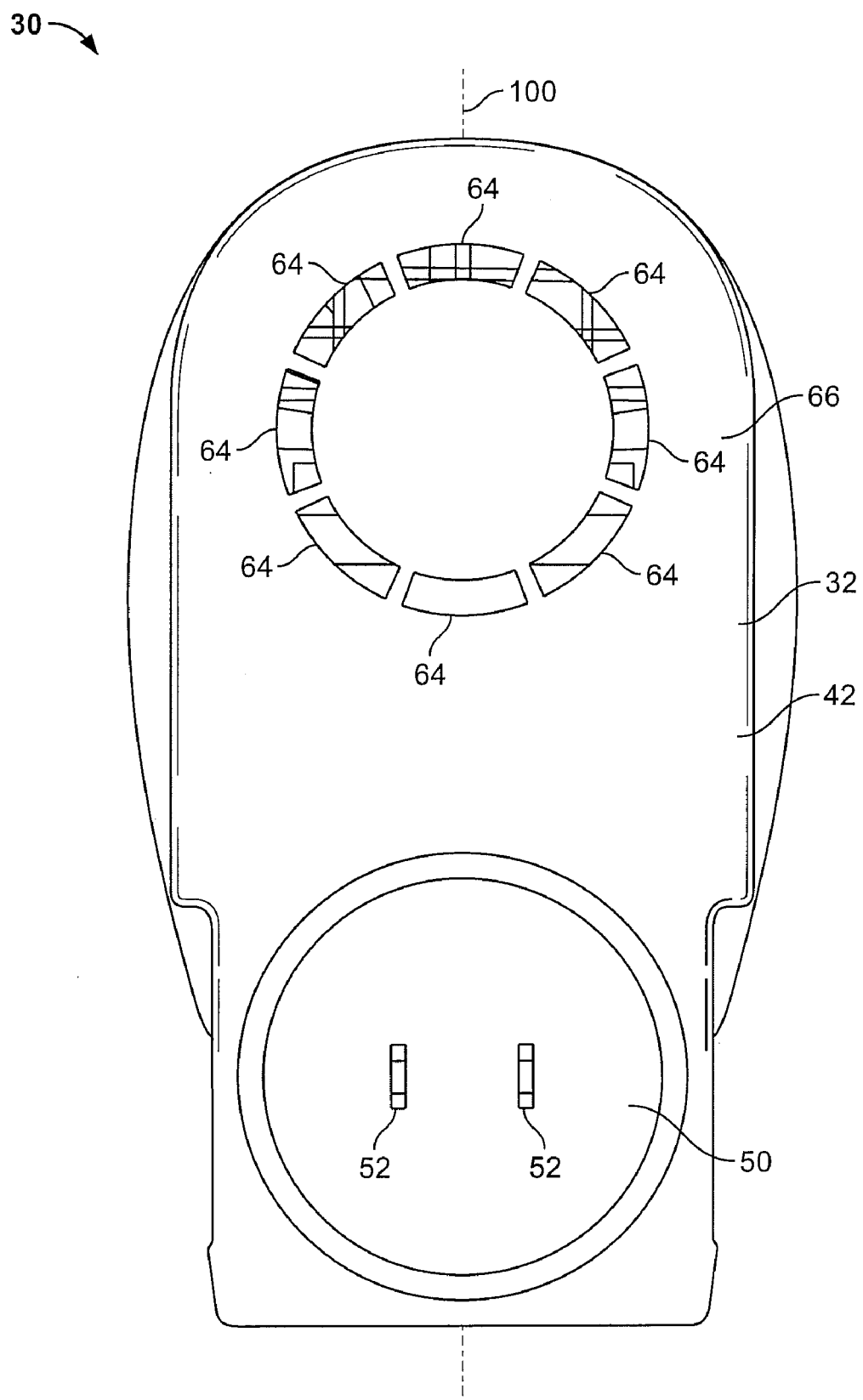
FIG. 4 is a rear elevational view of the diffusion device of FIG. 1.
Figure 5:
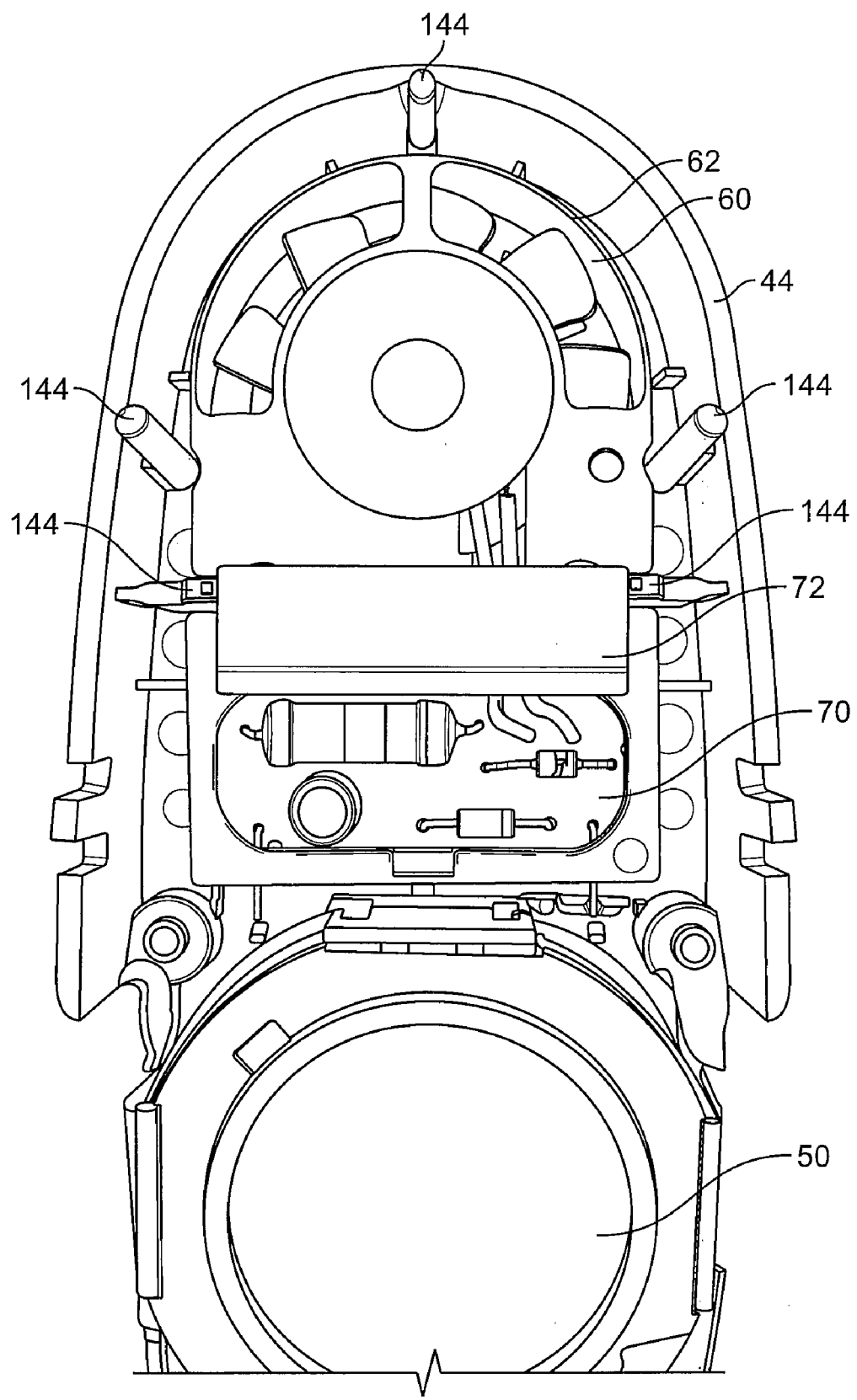
FIG. 5 is a top perspective view of a first shell portion of a rear portion of a housing of the diffusion device of FIG. 1.
Figure 10:
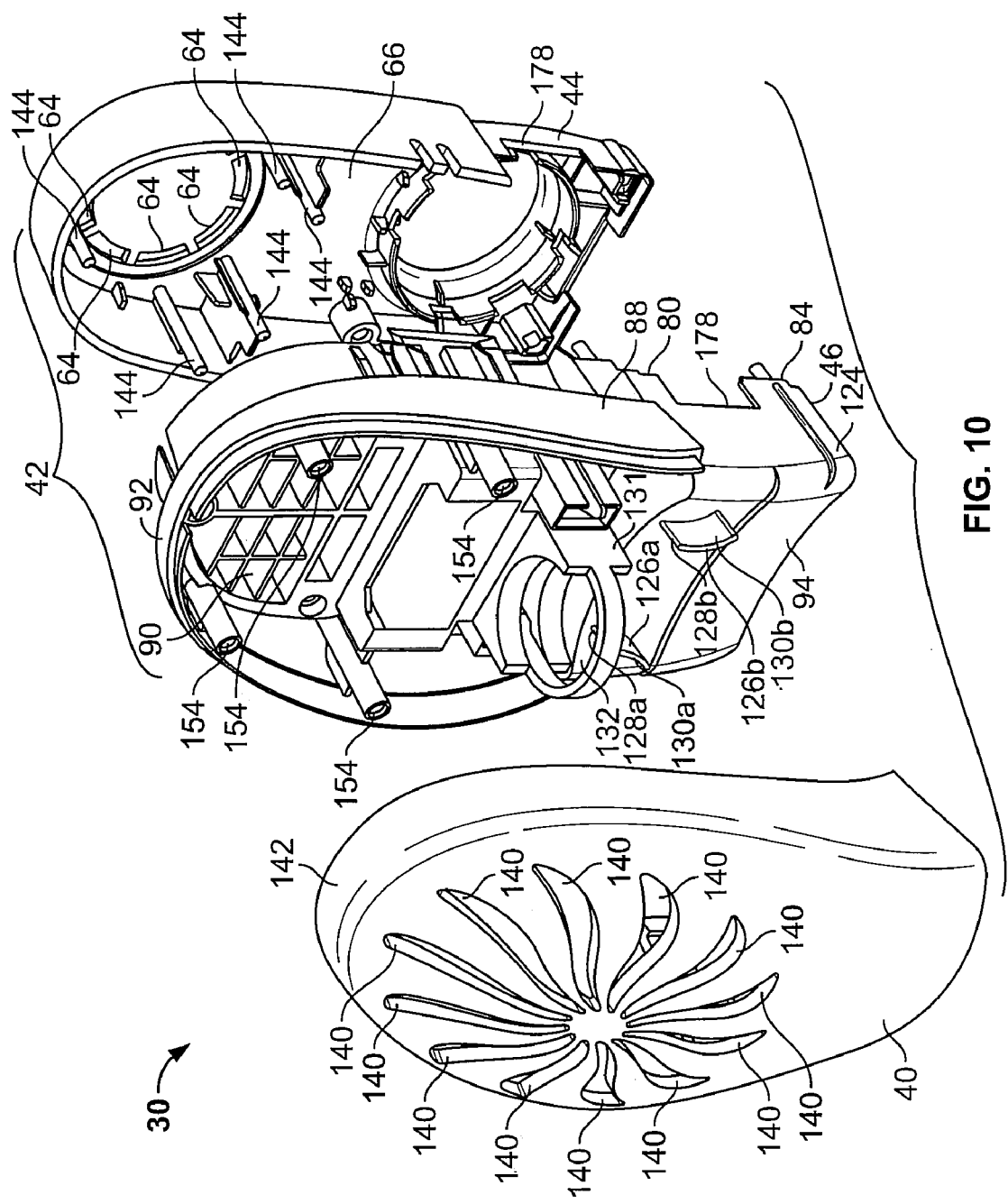
FIG. 10 is an exploded view of the diffusion device of FIG. 1 with electrical components removed therefrom.

As seen in FIG. 5, a casing 58 is disposed within the first shell portion 44 above the plug assembly 50. A fan unit 60 is disposed within an upper portion 62 of the casing 58. As seen in FIGS. 4 and 10, a plurality of air inlets 64 are disposed through a rear surface 66 of the first shell portion 44 for supplying air to the fan unit 60. Referring again to FIG. 5, a circuit board 70 for controlling the electrical components of the device 30 is disposed within the casing 58 below the fan unit 60 and a heater 72 is disposed adjacent and electrically connected to the circuit board 70 by wires 73 (FIG. 11), wherein the heater 72 is also disposed below the fan unit 60. During operation of the device 30, the heater 72 may run continuously and the fan unit 60 may also run continuously.

Figure 6:
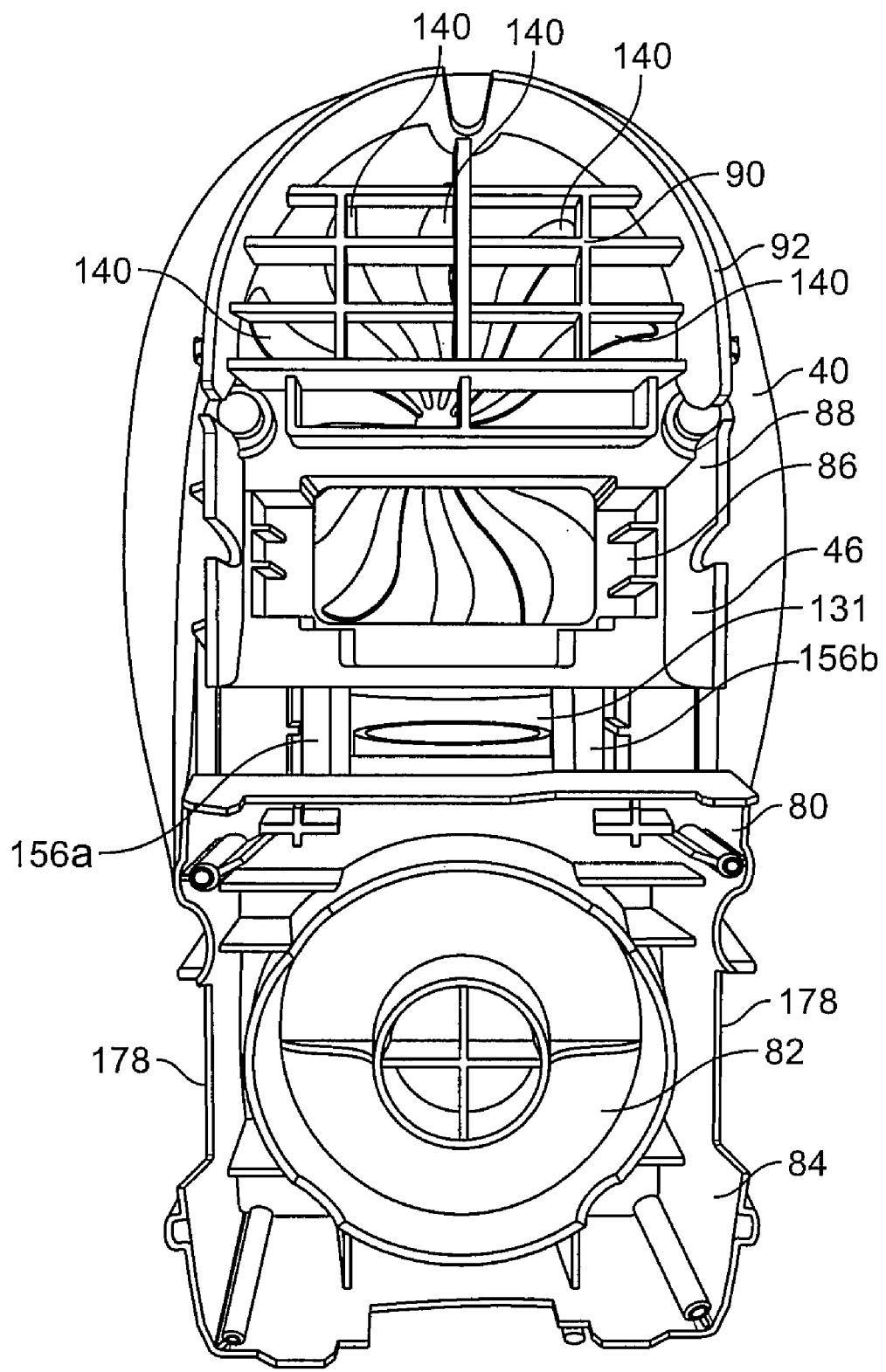
FIG. 6 is a rear perspective view of a second shell portion of the rear portion of the housing of the diffusion device of FIG. 1.

Referring to FIG. 6, a first side 80 of the second shell portion 46 includes a guide 82 at a bottom portion 84 thereof for guiding the plug assembly 50 during rotation thereof. A cavity 86 is also disposed within a central portion 88 of the first side 80 of the second shell portion 46. When the first and second shell portions 44, 46 are attached to one another, the heater 72 is disposed within the cavity 86. A set of louvers 90 is disposed in an upper portion 92 of the second shell portion 46. The louvers 90 extend between the first side 80 and a second opposing side 94 of the second shell portion 46. The louvers 90 are illustratively transverse to an orientation axis 100 of the device 30 such that air from the fan unit 60 is directed in a generally horizontal direction when the device 30 is in an operative position.

Figure 7:
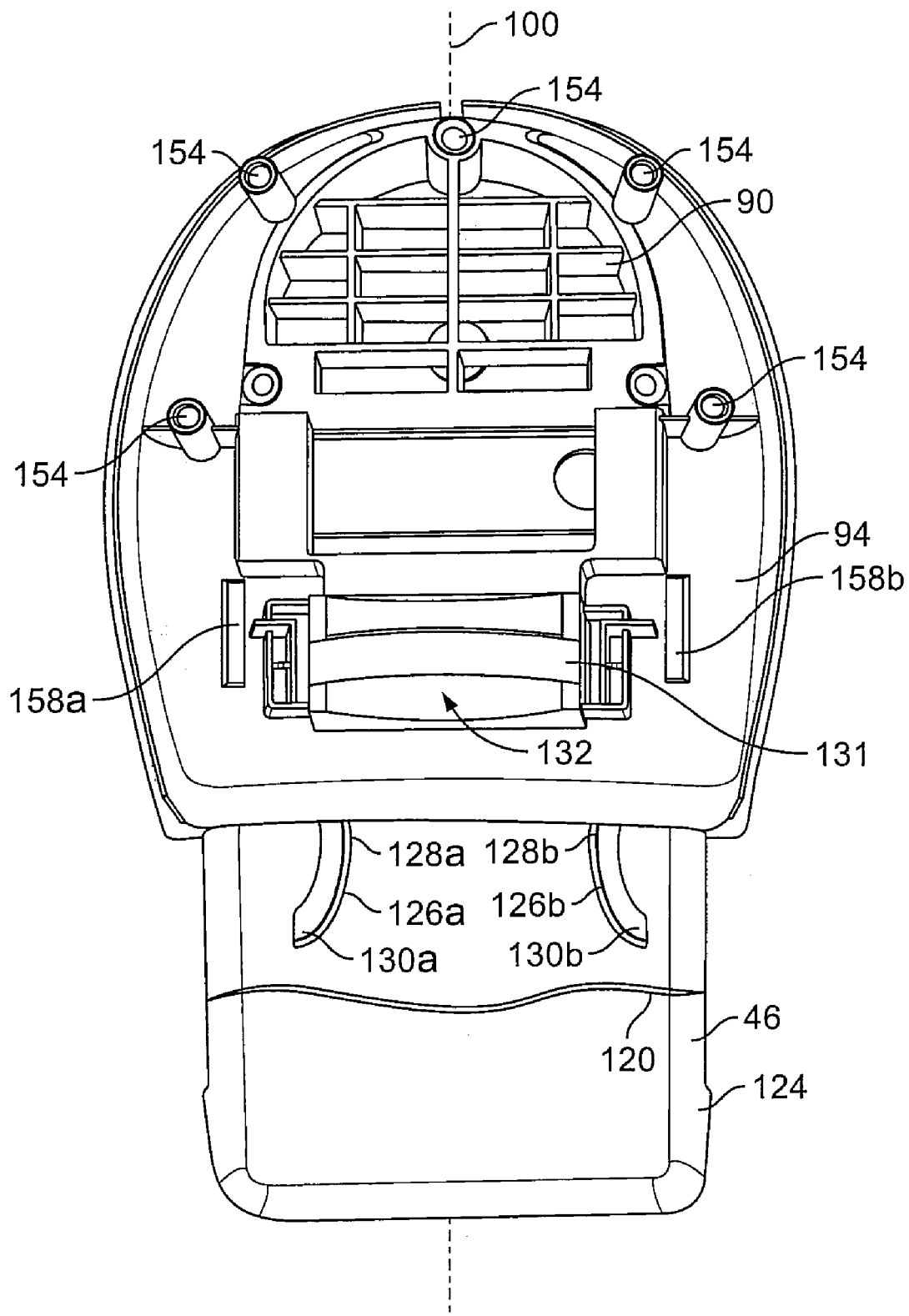
FIG. 7 is a front trimetric view of the second shell portion of the rear portion of the housing of the diffusion device of FIG. 1.
Figure 11:
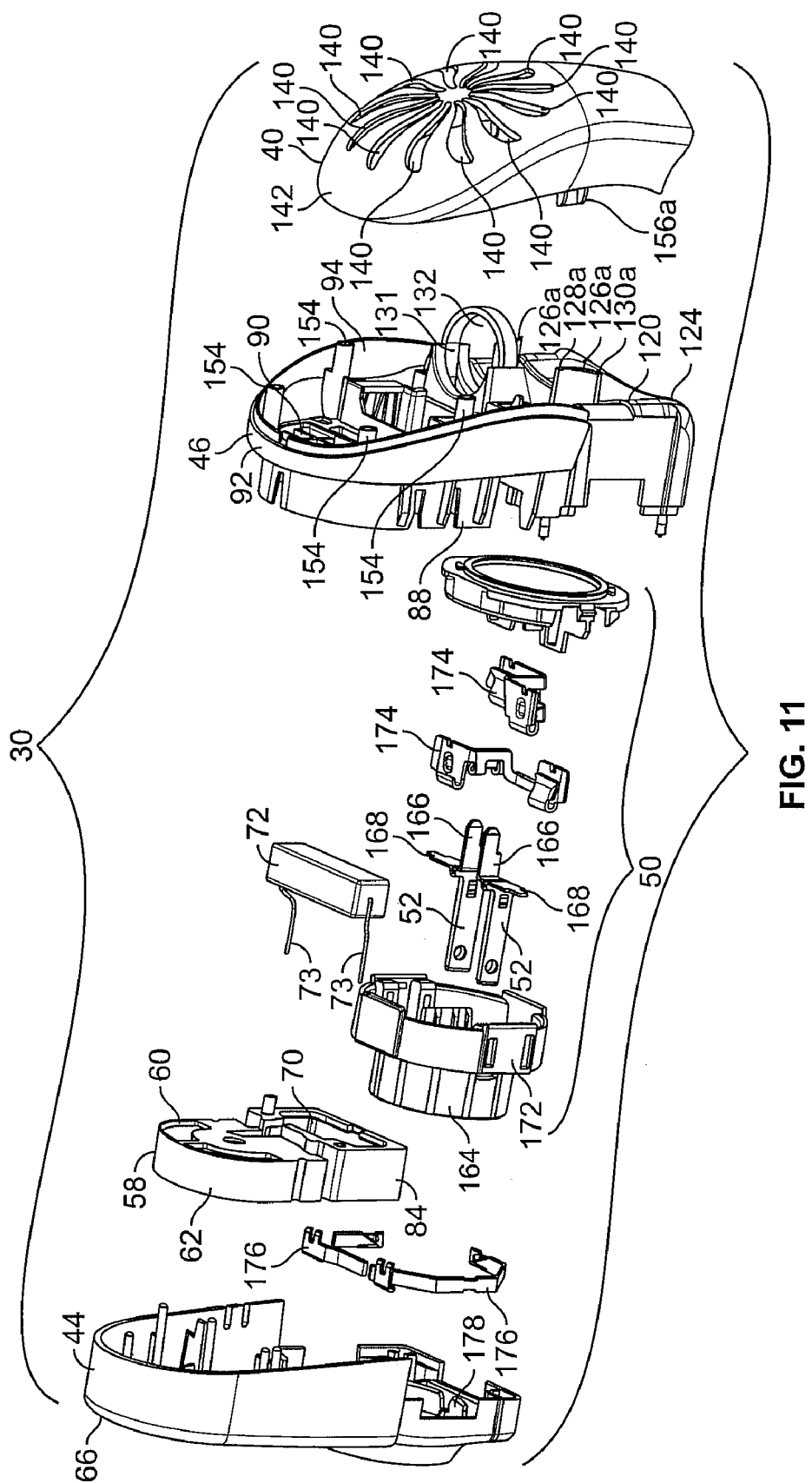
FIG. 11 is an exploded view of the diffusion device of FIG. 1.

A retention ledge 120 is formed in a bottom portion 124 of the second side 94 of the second shell portion 46, as seen in FIGS. 1-3, 7, and 9-11. The ledge 120 interacts with the container 34 to aid in retaining the container 34 within the device 30. Such interaction will be discussed in greater detail hereinafter. First and second opposing projections 126a, 126b extend from the second side 94 of the second shell portion 46 and are disposed above the retention ledge 120. The projections 126a, 126b include upper portions 128a, 128b and lower portions 130a, 130b, wherein the projections 126a, 126b curve outwardly from the upper portions 128a, 128b to the lower portions 130a, 130b. The projections 126a, 126b may take any form that sufficiently fulfills the purpose thereof. A third projection 131 extends outwardly from the second side 94 of the second shell portion 46, as best seen in FIGS. 7, 10, and 11. The third projection 131 includes a circular aperture 132 therethrough. The purpose and functionally of the retention ledge 120, the first and second projections 126a, 126b, and the third projection 131 will be discussed in greater detail hereinafter.

Figure 2:
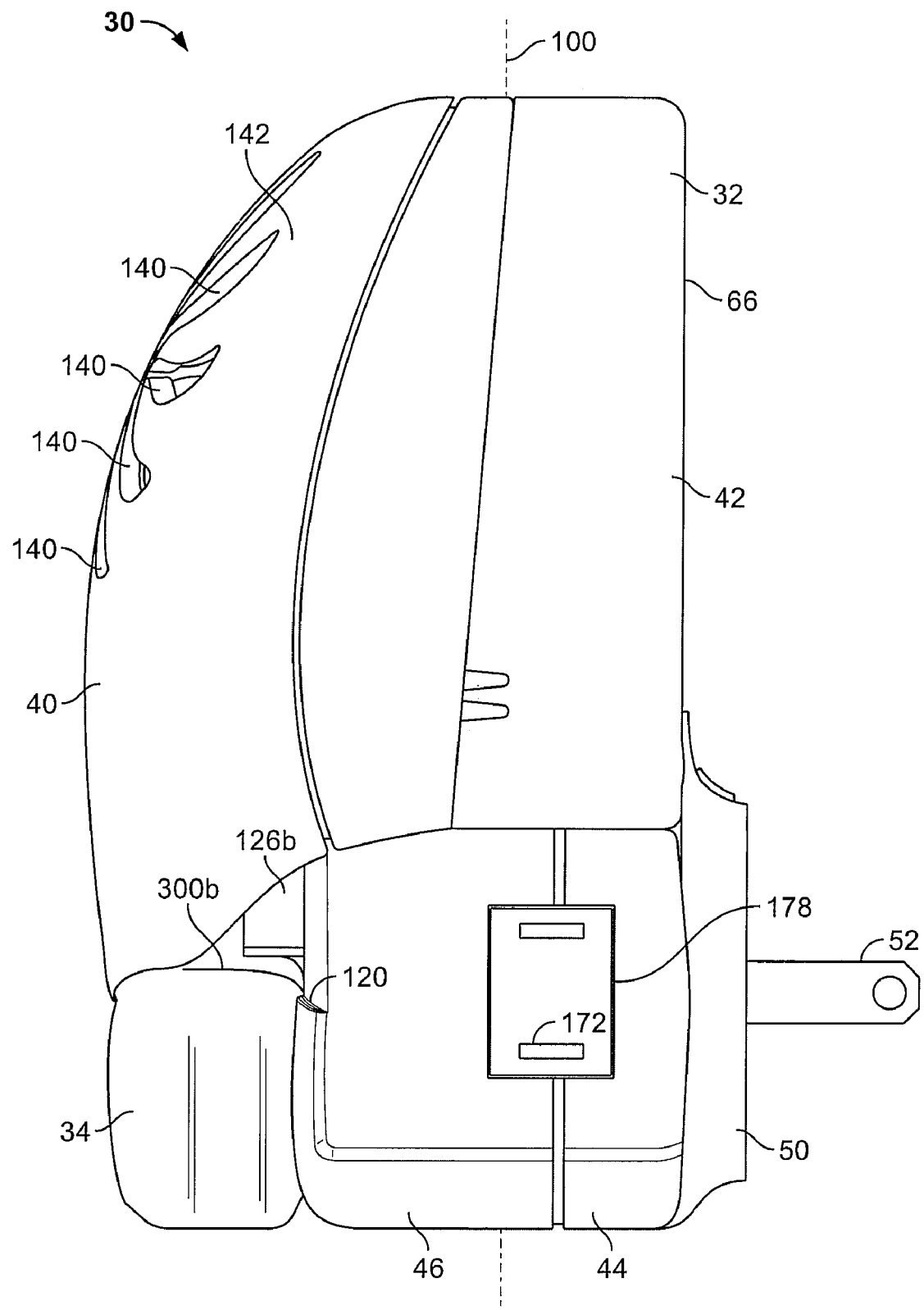
FIG. 2 is a side elevational view of the diffusion device of FIG. 1.
Figure 3:
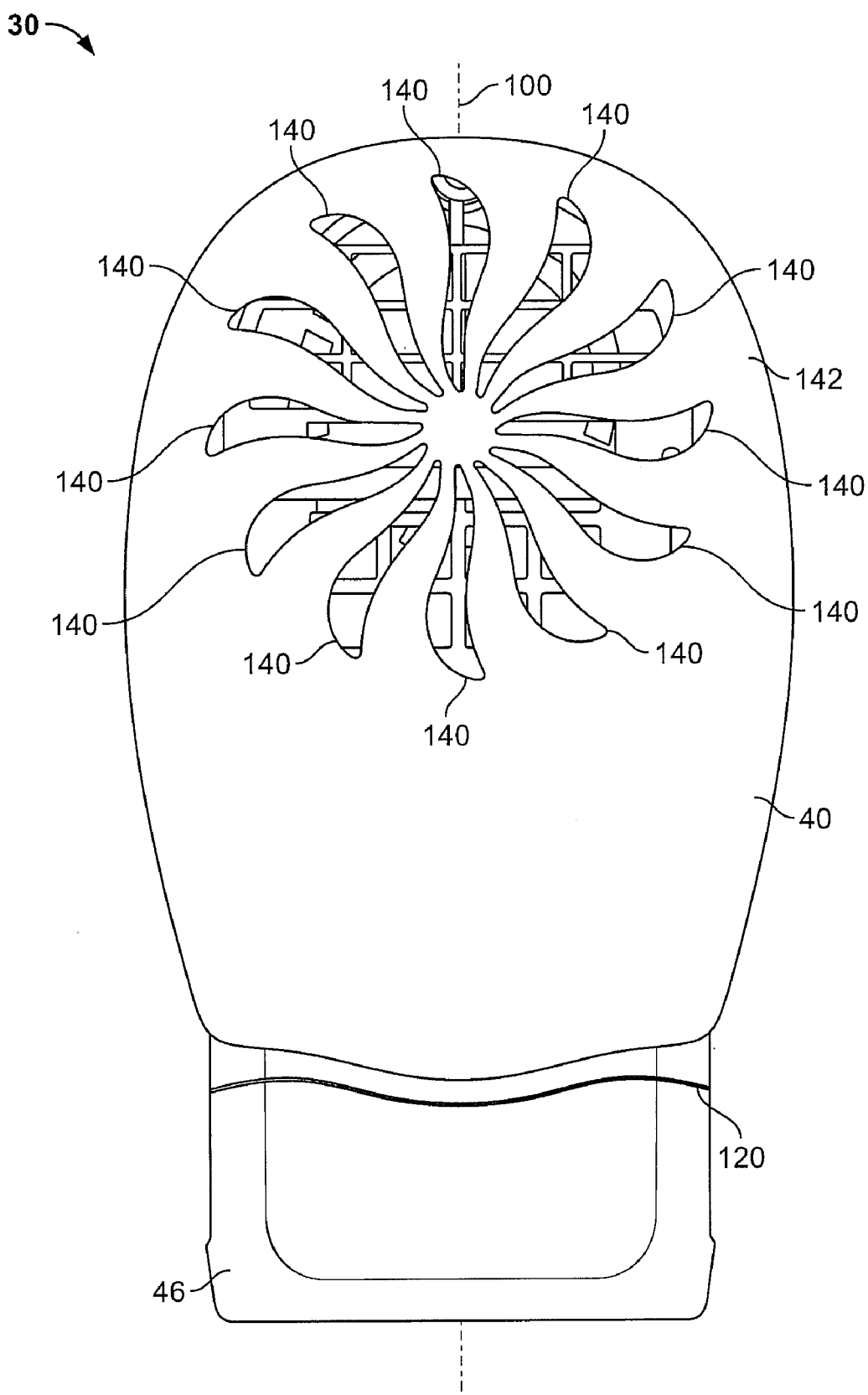
FIG. 3 is a front elevational view of the diffusion device of FIG. 1.
Figure 4A:
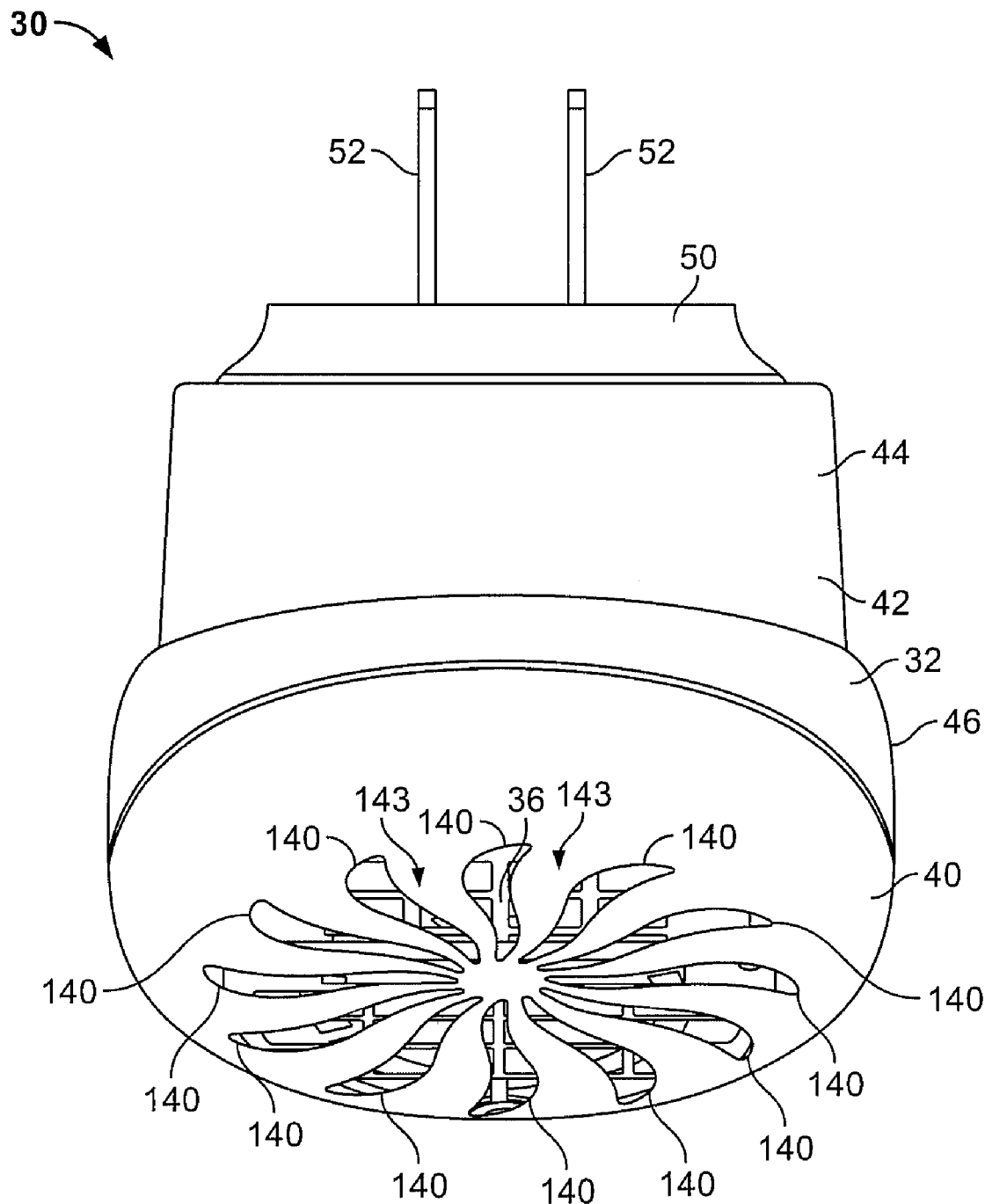
FIG. 4A is a plan view of the diffusion device of FIG. 1.

As seen in FIGS. 1-3, 8, 10, and 11, the front portion 40 of the housing 32 forms a cover for the first and second shell portions 44, 46 of the rear portion 42 of the housing 32. The front portion 40 includes a plurality of vents 140 disposed therethrough but, as best seen in FIG. 2, the headspace above the top of the wick remains substantially enclosed. The vents 140 are disposed at an upper portion 142 of the front portion 40 and opposing the fan unit 60 when the device 30 is assembled. As seen in FIG. 4A, the wick 36 is substantially enclosed by the front portion 40. In particular, the wick 36 has a cross-sectional size and shape in a horizontal plane that is transverse to the orientation axis 100 of the device 30, wherein the cross-sectional size and shape of the wick 36 in a horizontal plane is less than a cross-sectional size and shape in a horizontal plane of any one of the vents 140.

As best seen in FIG. 4A, active material diffusion-interference members 143 are formed by the front portion 40 of the housing 32 directly above and axially aligned with at least a portion of the wick 36. Although not wishing to be bound by theory, it is believed that the diffusion-interference members 143 obstruct and/or inhibit diffusion of active material from within the housing 32 to an area outside the device 30, and therefore trap heat within the housing 32, which results in an overall increase in temperature surrounding the wick 36. By increasing the temperature surrounding the wick 36, the overall diffusion of the active material from the diffusion device 30 increases because, for example, the increase in temperature more quickly volatilizes the active material, thereby causing a build-up of active material within the device. In order to accommodate this increase in volatilized material within the device 30, some of the volatilized active material is therefore pushed upwardly between the fan unit 60 and the vents 140 and dispersed into the surroundings by same. This effect was not previously recognized by those skilled in the art.

Although the diffusion-interference members 143 are depicted as members extending between the vents 140, the diffusion interference members 143 may take any form that would inhibit immediate movement of active material from the wick 36 directly into the surroundings. For example, the front portion 40 of the housing 32 may be vertically aligned and vents 140 may be formed in the front portion 40, but such vents 140 would not be disposed above the wick 36. In such embodiment, a top portion of the device 30 would not include any vents, and thus the top portion would constitute an active material diffusion-interference member 143 because the top portion would inhibit vaporized active material from streaming upwardly and out of the device 30.

Figure 8:
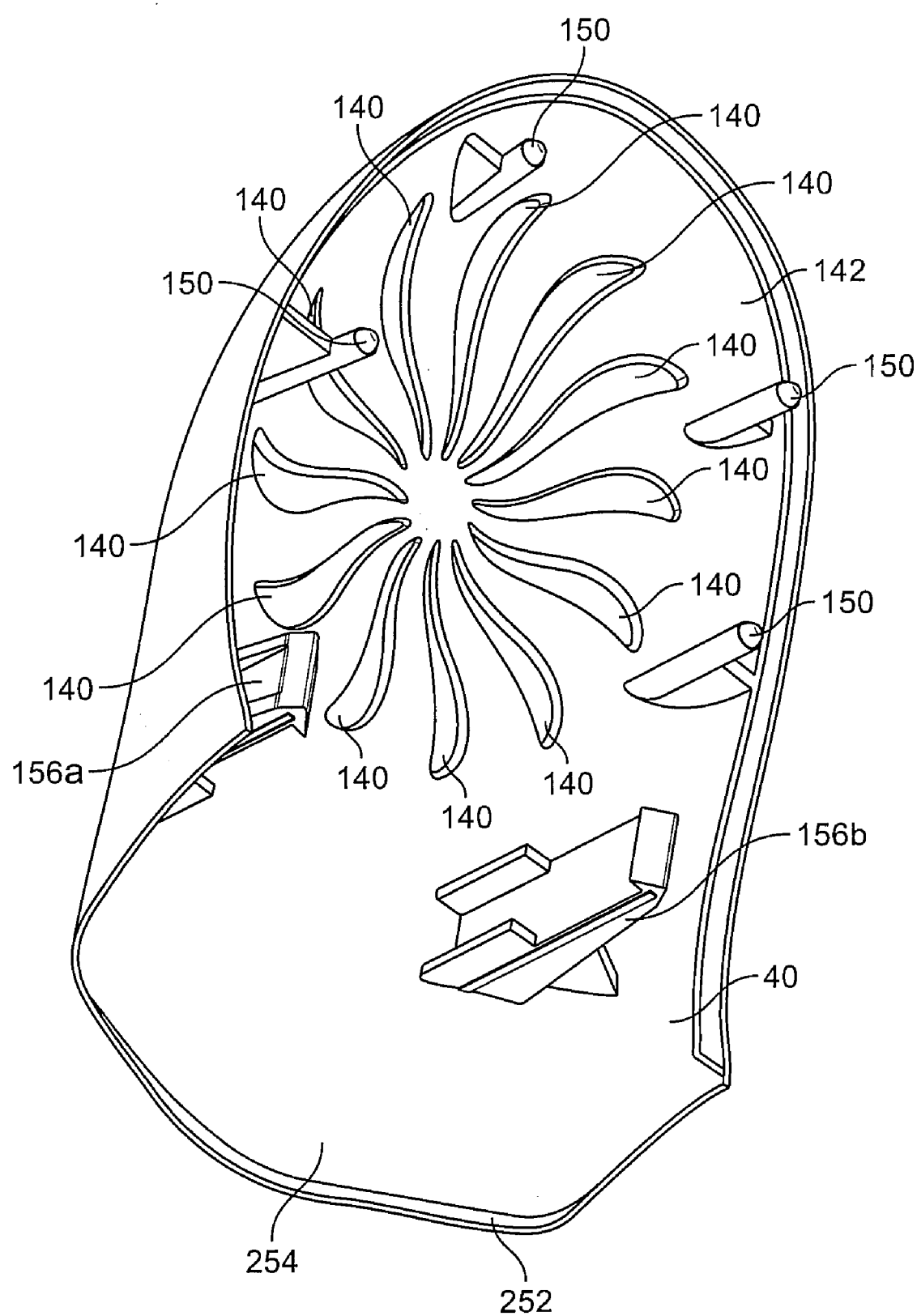
FIG. 8 is a rear trimetric view of a front portion of the housing of the diffusion device of FIG. 1.
Figure 9:
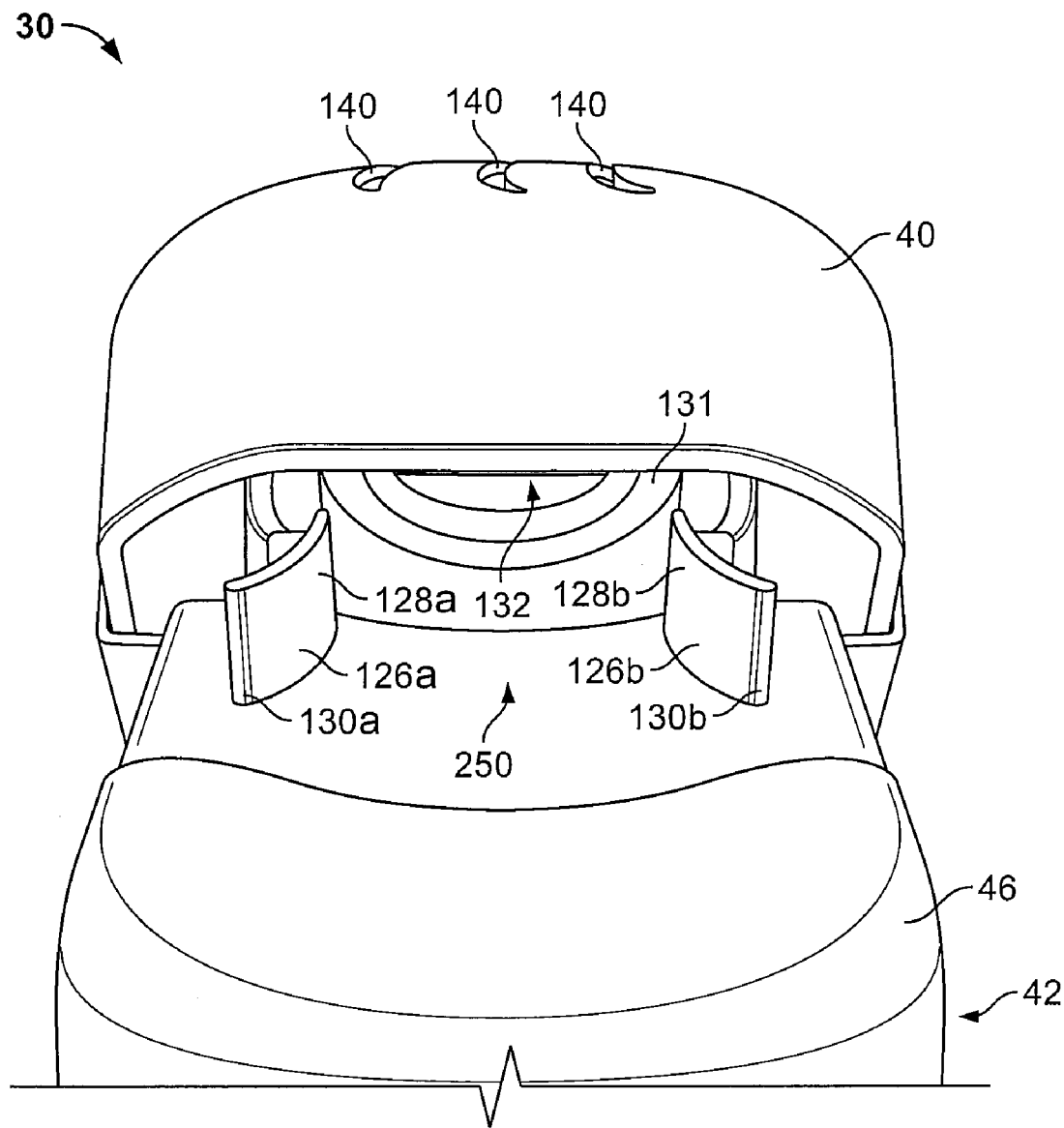
FIG. 9 is a bottom trimetric view of the diffusion device of FIG. 1.

As seen in FIGS. 10 and 11, the first and second shell portions 44, 46 of the rear portion 42 may be permanently attached to one another by a plurality of posts 144 extending from the first shell portion 44, wherein the posts 144 are heat staked to the second shell portion 46 during manufacture and assembly of the device 30. When the first and second shell portions 44, 46 are assembled, the heater 72 is disposed within the cavity 86 in the second shell portion 46 and the louvers 90 are disposed adjacent the fan unit 60. As seen in FIG. 8, a plurality of cylindrical projections 150 extend from a rear surface 152 of the front portion 40 and are secured within a plurality of standoffs 154 extending from the second side 94 of the second shell portion 46 to aid in retaining the front portion 40 on the rear portion 42. In addition, a pair of arms 156a, 156b extends from the rear surface 152 of the front portion 40 and engage grooves 158a, 158b formed on sides of the third projection 131 extending from the second shell portion 46 to further retain the front portion 40 on the rear portion 42. In this embodiment, once the device 30 has been assembled, it is provided to a consumer such that disassembly is difficult.

Referring to FIG. 11, the plug assembly 50 includes a stepped, cylindrically-shaped body 160. The blades 52 protrude through narrow slits (not shown) in a rear face 164 of the plug assembly body 160, in a direction parallel to an axis of rotation of the plug assembly 50. Each plug blade 52 includes a spring contact 166 at its distal end and a sliding contact 168. The sliding contacts 168 protrude slightly through openings 170 (only one shown) provided on opposite sides of the plug assembly body 160. The plug blades 52, including the spring contacts 166 and sliding contacts 168, may be made of nickel-plated brass, although other well-known conductive materials could also be utilized.

The plug assembly 50 includes at least one, or two, extra outlets 172, as shown in FIGS. 1, 2, and 11, a pair of rigid conductive members 174 are press fit over the spring contacts 166, thereby electrically connecting the extra outlets 172 to the plug blades 52. The conductive members 174 are made of brass, although other well-known conductive materials could also be used.

The plug assembly 50 rotates within the guide 82 of the second shell portion 46. A pair of contact carriers 176 is fixed within the housing 32, substantially surrounding a cylindrical surface of the plug assembly 50, as seen in FIG. 11. The contact carriers 176 are made of phosphor bronze, but other well-known conductive materials could also be utilized. The contact carriers 176 selectively provide an electrical connection between the plug assembly 50 and the electrical components of the diffusion device 30. The first shell portion 44 of the housing 32 may include windows 178 (FIGS. 1, 2, 6, 10, and 11) that correspond with the extra outlets 172 such that the extra outlets 172 may be accessed. The rotatable plug assembly 50 may be similar to that disclosed in Pedrotti et al. U.S. Pat. No. 6,862,403, the disclosure of which is incorporated by reference herein.

Figures 12, 13:
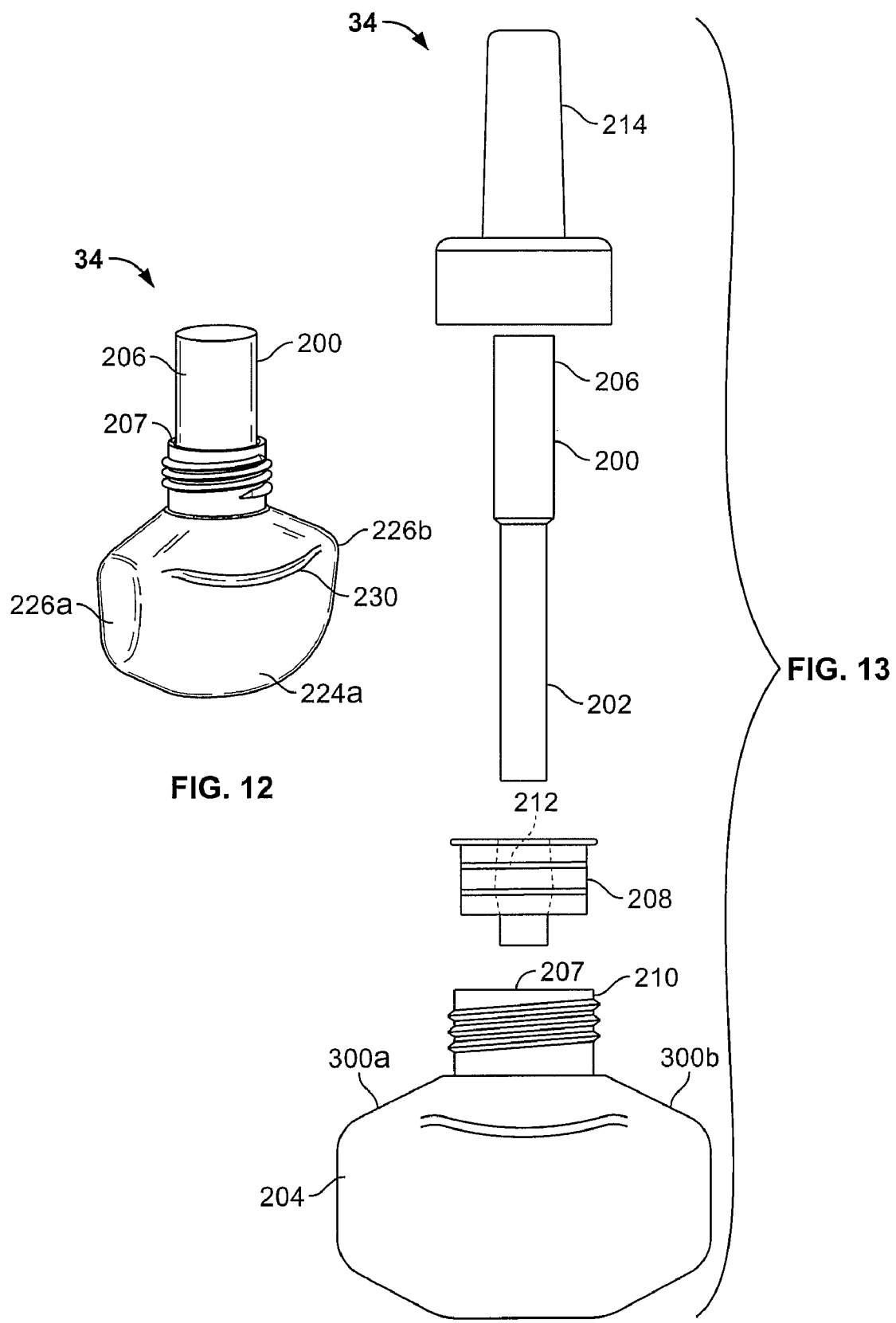
FIG. 12 is a front isometric view of a container for holding a liquid active material for use with the diffusion device of FIG. 1.
FIG. 13 is an exploded view of the container of FIG. 12.
Figure 14:
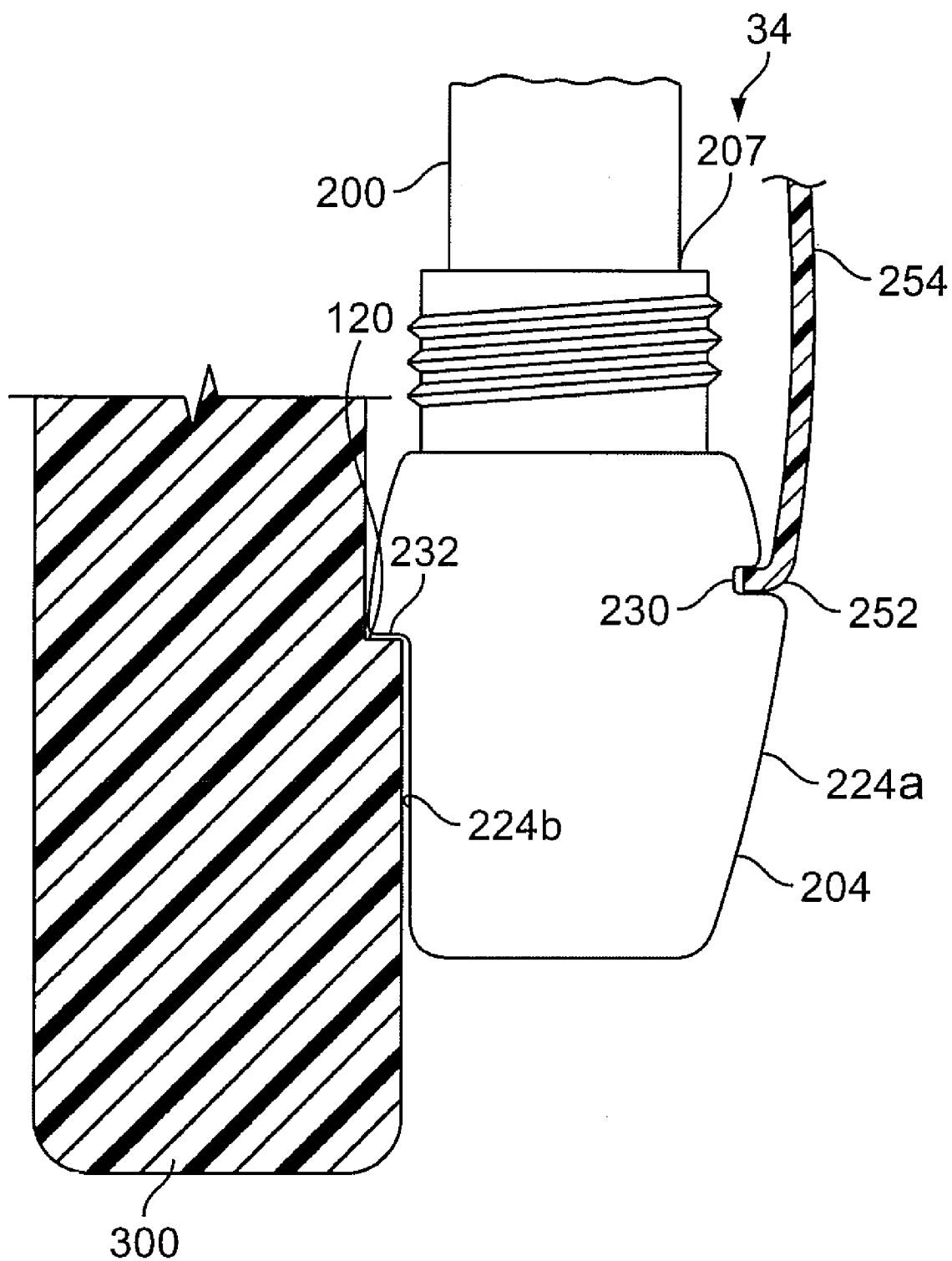
FIG. 14 is a side elevational view of the container of FIG. 12 illustrating the manner in which the container is retained within the diffusion device of FIG. 1.

As shown in FIGS. 12-14, the container 34 includes a wick or capillary member 36 with a first end 202 disposed within the container 34 in contact with a liquid active material within the container 34 and a second end 206 that extends out of the container portion 34 through an opening 207. A neck closure 208 is disposed within a neck 210 of the container 34 and includes a channel 212 through which the wick 36 extends and the neck closure 208 retains the wick 36 within the container 34. The container 34 further includes a cap 214 connected to the neck 210 of the container 34 for shipping and storing the container 34. The cap 214 is removed before inserting the container 34 into the device 30.

Referring to FIG. 12, the container 34 is formed by first and second opposing longitudinal sidewalls 224a, 224b having a concave curvature and first and second opposing lateral sidewalls 226a, 226b connecting the longitudinal sidewalls 224a, 224b. A recess 230 (FIG. 14) is disposed in the first longitudinal sidewall 224a and a downwardly facing ledge 232 (FIGS. 12 and 14) is formed in the second longitudinal sidewall 224b of the container 34. The recess 230 is disposed higher in the sidewall 224a than the ledge 232 is disposed in the sidewall 224a, such that the recess 230 is closer to the opening 207 than the ledge 232.

The cap 214 is removed from the container 34 and the container 34 is releasably secured to the dispensing device 30 by inserting the wick 36 of the container 34 into an interior cavity 250 (FIG. 9) formed between the front portion 40 and the second shell portion 46 of the rear portion 42 and through the aperture 132 of the third projection 131 and pushing the container 34 upwardly into the dispensing device 30. As seen in FIGS. 8 and 14, an inward projection 252 formed by a lower portion 254 of the front portion 40 engages walls defining the recess 230 in the first longitudinal sidewall 224a of the container 34 and the retention edge 120 of the second shell portion 46 engages the ledge 232 in the container 34 to retain the container 34 within the dispensing device 30. As seen in FIG. 2, the first and second projections 126a, 126b prevent further upward movement of the container 34 so that the wick 36 is not damaged during insertion of the container 34 into the device 30. In particular, the projections 126a, 126b are disposed adjacent upper shoulders 300a, 300b (FIGS. 2 and 13) of the container 34 when the container 34 is inserted into the device 30 and interfere with the shoulders 300a, 300b to prevent upward movement of the container 34.

The container 34 is removed from the dispensing device 30 by pulling the container 34 away from the interior cavity 250. As the container 34 is pulled, the walls defining the recess 230 and the ledge 232 and the lower portion 254 of the front portion 40 of the housing 32 flex outwardly, thereby allowing removal the container 34.

Illustratively, and as seen in FIG. 4A, when the container 34 is fully inserted into the device 30, none of the vents 140 has a horizontal cross-sectional size or shape in a horizontal plane that is substantially equivalent to or larger than a cross-sectional size and shape in a horizontal plane of the wick 36. Such a vent configuration, alone or in combination with the active material diffusion-interference members 143, increases the evaporation efficiency and weight loss of the device 30, as will be discussed in greater detail hereinafter.

The container 34 and the mechanism for retaining the container 34 within the device 30 are discussed in greater detail in Duston et al. U.S. Pat. No. 7,032,831 and Kotary et al. U.S. Publication No. 2004/0184969, the disclosures of which are incorporated by reference herein.

A method of increasing the volatilization of an active material is also provided. The method includes in one embodiment, the step of providing a diffusion device 30 having a housing 32 and fan unit 60 and/or a heater 72. The method further includes the step of inserting a container 34 having a wick 36 extending therefrom into the device 30. Still further, the method includes the step of providing an active-material diffusion-interference member 143 in the housing 32 directly above and axially aligned with the wick 36 to inhibit or obstruct the diffusion of volatile material from within the housing 32 to an area outside the housing 32.

A further method of increasing the volatilization of an active material is also provided. The method includes in this embodiment, the step of providing a diffusion device 30 having a housing 32 and fan unit 60 and/or a heater 72. The method further includes the step of inserting a container 34 having a wick 36 extending therefrom into the device 30. Still further, the method includes the step of providing a vent 140 within the housing 32, wherein the vent 140 has a cross-sectional size and shape in a horizontal plane that is smaller than a cross-sectional size and shape in a horizontal plane of the wick 36.

Figure 17:
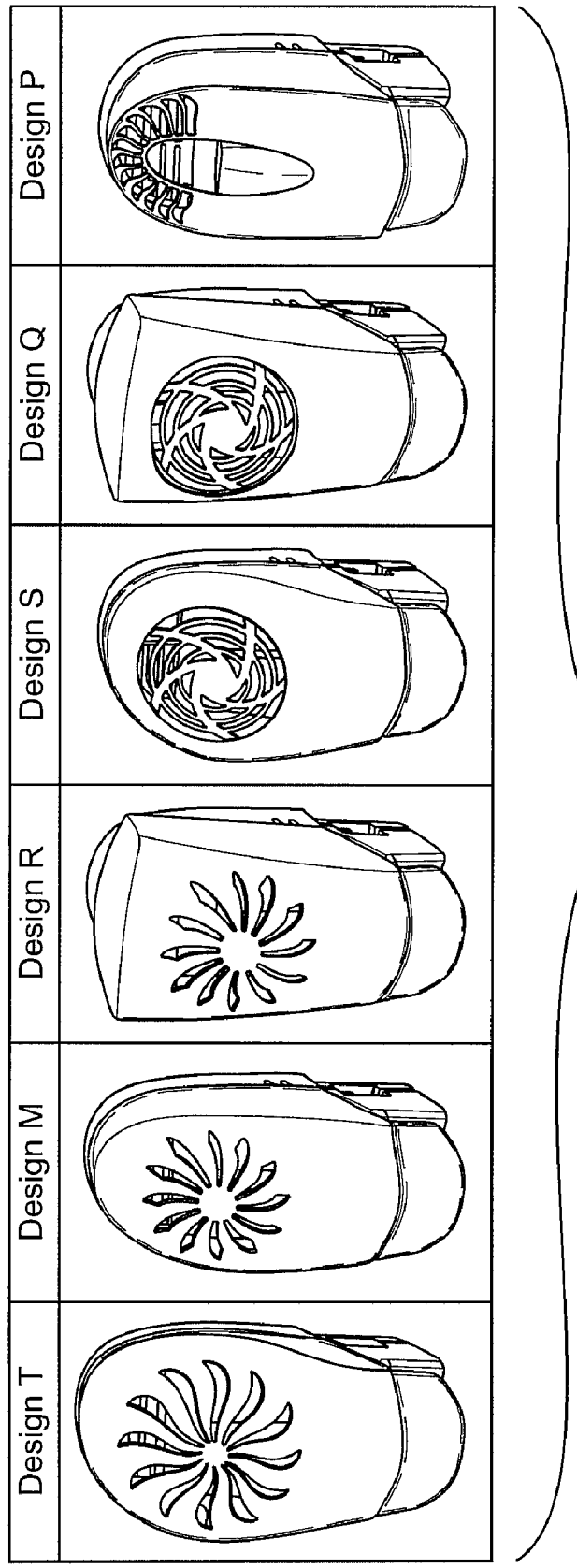
FIG. 17 is a diagram showing various design configurations utilized in the second testing protocol.

Diffusion devices were tested for their ability to increase the rate of diffusion of a volatile active material from the device 30. The devices tested are shown in FIG. 17 and all include louvers 90 with a generally horizontal orientation and further include various configurations of vents 140. Unit Nos. 1020, 1021, 1024, and 1025 are units having Design P of FIG. 17, where a vent having a cross-sectional size and shape in a horizontal plane substantially equivalent to or larger than a cross-sectional size and shape of a wick in a horizontal plane (or an "exposed wick") is disposed in a front portion thereof. Unit Nos. 1022, 1023, 1026, 1027, and 1075 are units having Design T, the unit described in detail herein. As described in detail herein, Design T is a "non-exposed" wick device. Unit Nos. 1071-1074 are units having Designs M, Q, R, and S, all of which are similar to Design T in that they do not include a vent having a cross-sectional size and shape in a horizontal plane substantially equivalent to or larger than a wick disposed therein. Designs M, Q, R, and S are only different in that they implement different vent patterns. Unit SCJ-088 is an S.C. Johnson commercial fan-based device sold under the name Oust® Fan and which is described in detail in Schwarz U.S. Publication No. 2006/0170119, the disclosure of which is hereby incorporated by reference. For each diffusion device, an "end-point" is defined as a time point when all but 2 grams of the original active material (11 grams to begin) has been evaporated and/or dispersed into the surroundings.

For all tests, the containers for each diffusion device were filled with 11 grams of active material and the weight loss in grams of the active material was measured against time. The containers and wicks utilized were identical to the container 34 and wick 36 as discussed in detail herein and which are discussed in detail in Kotary et al. U.S. Publication No. 2004/0184969 ("the '969 publication"), the disclosure of which is hereby incorporated by reference. Specifically, the containers are identical to that discussed with respect to FIG. 10 of the '969 publication. The containers and wicks are also commercially available as a refill for or as a set with the Oust® Odor-Free Fan, both sold by S. C. Johnson of Racine, Wis. wherein the only scent utilized for all tests was the Oust® citrus scent.

In a first test, (the results are shown below in Table 1 and FIG. 15), multiple sample diffusion devices were tested, wherein various factors were tested. All samples included a fan and samples 1-12 also included a heater. In particular, all fans are 12V, DC, brushless Axial fans with a product description code of 16523—FNM-ELE-120V, which are manufactured and sold by Power Logic Tech Inc. of Taipei Hsien, Taiwan, wherein the fan has a velocity of 2400 rotations per minute. All heaters are 7W metal oxide resistor heaters manufactured and sold by Great Land Enterprise Co., Ltd. of Shenzhen, China, wherein the heater has a temperature of 89 degrees Celsius. Samples 1-4 included heaters in a first position (disposed 2.65 mm behind the wick) and samples 5-8 included heaters in a second position (disposed 9 mm behind the wick). Each different heater position was tested with "exposed" and "non-exposed" wicks and with both 1.9 kOhm and 2.9 kOhm heaters.

Figure 15:
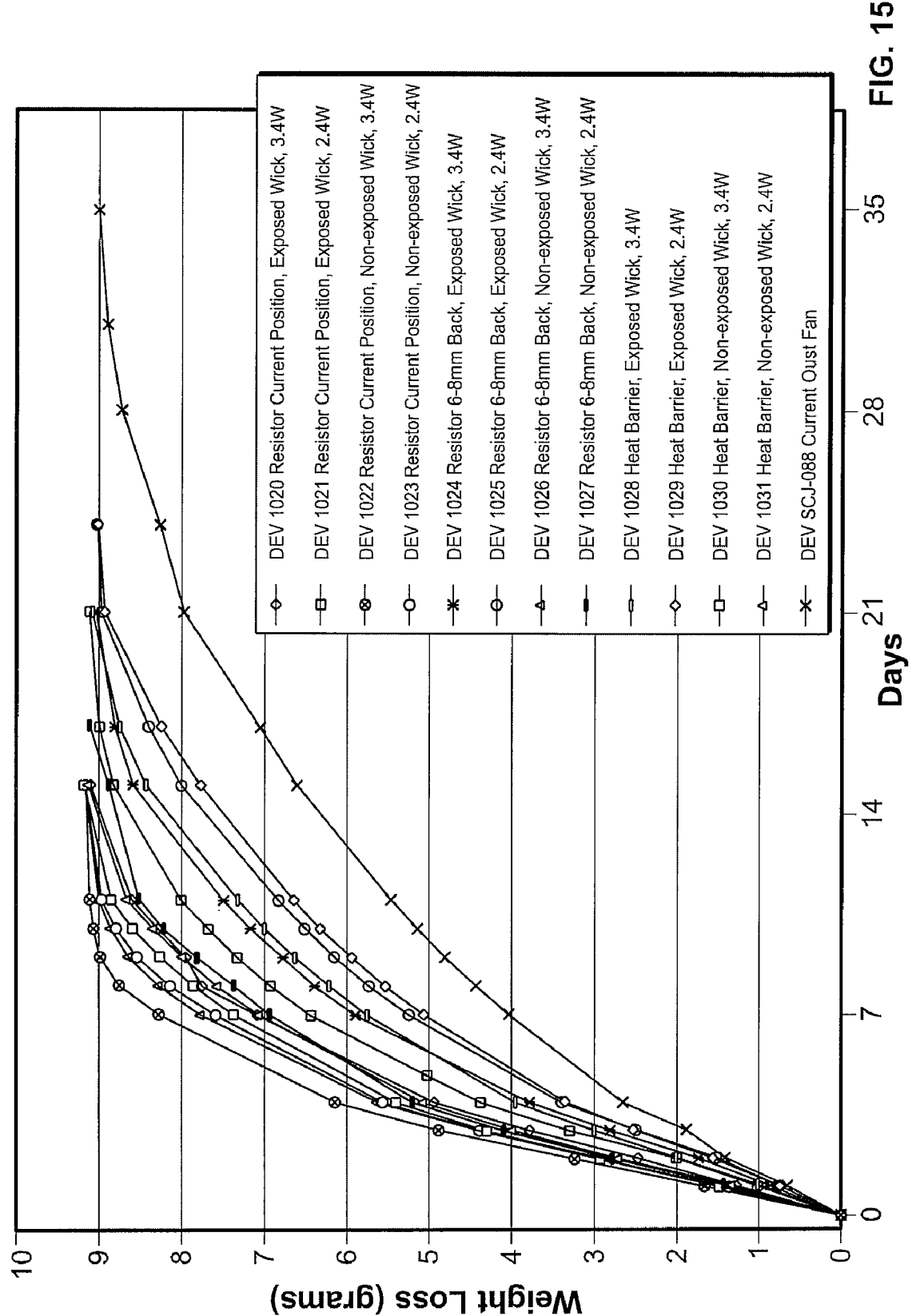
FIG. 15 is a graph depicting results of a first testing protocol.

Referring to Table 1 and FIG. 15 and comparing the devices with "exposed" wicks against the devices with "non-exposed" wicks, in all cases, the devices with "non-exposed" wicks resulted in greater volatilization and greater weight loss of the active material and met their end-point before the "exposed" wicks in substantially identical devices. Sample 9 included only a fan and was used in this testing protocol to generally show the weight loss over time of the active material using only a fan. As would be expected, the active materials disposed within the samples having both a heater and a fan (samples 1-12) had a greater weight loss over time than sample 9, which only had a fan.

TABLE 1

| Sample | Unit # | Heater Design/ Description | Front Design/ Setting | K Ohm (Heater) | Fragrance | End-Point (Days) |
| --- | --- | --- | --- | --- | --- | --- |
| 1 | 1020 | Resistor in current position | Exposed Wick | 1.9 | Oust Citrus | 14 |
| 2 | 1021 | Resistor in current position | Exposed Wick | 2.9 | Oust Citrus | 17 |
| 3 | 1022 | Resistor in current position | Non-Exposed Wick | 1.9 | Oust Citrus | 9 |
| 4 | 1023 | Resistor in current position | Non-Exposed Wick | 2.9 | Oust Citrus | 12 |
| 5 | 1024 | Resistor 6-8 mm back | Exposed Wick | 1.9 | Oust Citrus | 20 |
| 6 | 1025 | Resistor 6-8 mm back | Exposed Wick | 2.9 | Oust Citrus | 23 |
| 7 | 1026 | Resistor 6-8 mm back | Non-Exposed Wick | 1.9 | Oust Citrus | 11 |
| 8 | 1027 | Resistor 6-8 mm back | Non-Exposed Wick | 2.9 | Oust Citrus | 17 |
| 9 | SCJ-088 | Current Oust Fan | Current | | Oust Citrus | 34 |

Figure 16:
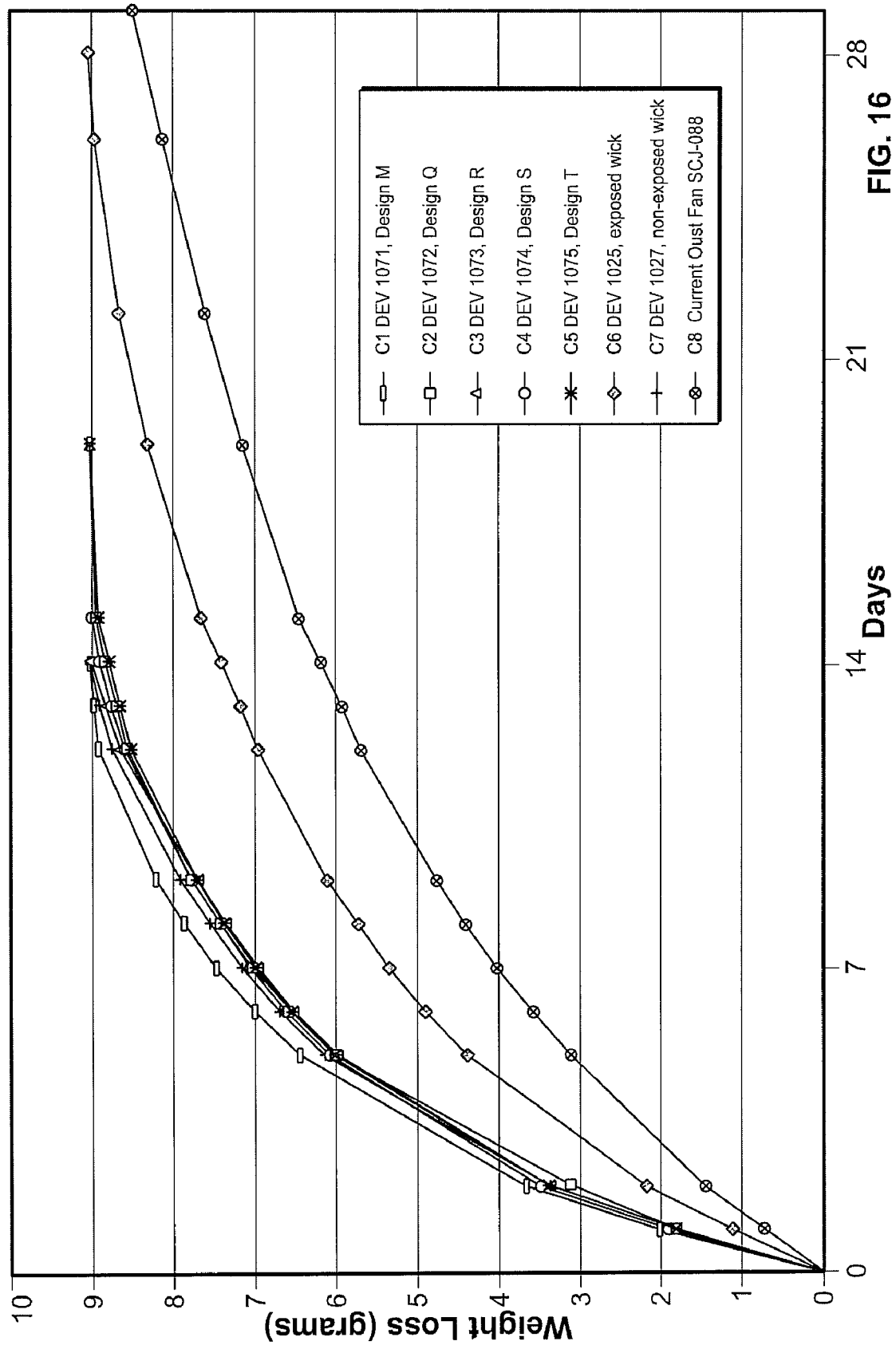
FIG. 16 is a graph depicting results of a second testing protocol.

A second test was performed, the results of which are shown in Table 2 below and the graph of FIG. 16. In the second test, the type of heater and the fragrance used were kept constant (and the same as the first test) for samples 1-7 and the configuration of vents was changed to determine a configuration for the vents that would optimize weight loss, and therefore efficiency. In particular, samples 1-5 and 7 had "non-exposed" wicks and included designs corresponding to the designs as seen in FIG. 17. Sample 6 had an "exposed" wick and included the design configuration P as shown in FIG. 17. Sample 8 was again used to generally show the weight loss over time of the active material using only a fan. Referring to Table 2 and the graph of FIG. 16, the devices having "non-exposed" wicks all had a greater weight loss and the active materials therein met their end-point before the device with the "exposed" wick. Additionally, as would be expected, all samples having both a heater and a fan had a greater weight loss than sample 8, which only included a fan.

The overall conclusion of the second test was that, no matter what vent design configuration is used, the "non-exposed" wick devices increase volatilization and create a greater weight loss over time of the active material from the device compared to "exposed" wick devices.

TABLE 2

| Sample | Unit # | Heater Design/ Description | Front Design | Fragrance | Estimated End-Point (Days) |
|---|---|---|---|---|---|
| 1 | 1071 | Resistor 6-8 mm back, 2.9 K | M | Oust Citrus | 14 |
| 2 | 1072 | Resistor 6-8 mm back, 2.9 watt | Q | Oust Citrus | 18 |
| 3 | 1073 | Resistor 6-8 mm back, 2.9 K | R | Oust Citrus | 14 |
| 4 | 1074 | Resistor 6-8 mm back, 2.9 K | S | Oust Citrus | 15 |
| 5 | 1075 | Resistor 6-8 mm back, 2.9 K | T | Oust Citrus | 18 |
| 6 | 1025 | Resistor 6-8 mm back, 2.9 K | Exposed Wick (P) | Oust Citrus | 27 |
| 7 | 1027 | Resistor 6-8 mm back, 2.9 K | M | Oust Citrus | 14 |
| 8 | SCJ-088 | Current Oust Fan | Current | Oust Citrus | 33 |

INDUSTRIAL APPLICABILITY

The present disclosure provides a device for emitting active materials therefrom, wherein the device has been designed to have an optimal weight loss. In particular, the devices includes one or more of a heater, a fan, a plurality of vents disposed opposite the fan, and a set of louvers disposed adjacent the fan. A container having a wick extending therefrom and an active material disposed therein is inserted into the device for dispersion of the active material. The wick is non-exposed in that there are no active material diffusion-interference members disposed directly above and axially aligned with the wick and/or any vents disposed above the wick have a cross-sectional size and shape in a horizontal plane that is smaller than a cross-sectional size and shape of the wick in a horizontal plane.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A diffusion device, comprising:
a housing;
an opening in the housing adapted for insertion of a container having an active material therein and a wick extending therefrom, wherein the wick has an axis extending along a length thereof;
a heater disposed in a rear portion of the housing and spaced from the wick when a container is inserted into the housing;
a vent disposed in a front portion of the housing;
an active material diffusion-interference member disposed directly above and aligned with the axis of the wick when the container is inserted into the device, wherein in use, the diffusion-interference member inhibits diffusion of the active material from the housing such that heat generated by the heater is trapped around the wick, thus increasing volatilization and dispersion of the active material from the diffusion device as compared to a diffusion device that does not have a diffusion-interference member and
a fan disposed in a rear portion of the housing opposite the vent and spaced from a top portion of the wick, wherein the fan moves vaporized active material out of the housing through the vent.

2. The diffusion device of claim 1, wherein a set of louvers is disposed adjacent the fan for directing air from the fan and through the housing.

3. The diffusion device of claim 2, wherein the louvers are oriented horizontally in an operative position to direct the airflow out the vent.

4. The diffusion device of claim 2, wherein the heater and the fan are spaced from one another along a vertical axis in an operative position such that active material vaporized by the heater is not immediately dispersed by the fan, but slowly moves into the airflow to be dispersed by the fan.

5. The diffusion device of claim 1, wherein a cross-sectional size and shape of the vent in a first horizontal plane formed through the vent is smaller than a cross-sectional size and shape of the wick in a second horizontal plane formed through the wick.

6. The diffusion device of claim 1, wherein the container is disposed within a front portion of the housing adjacent a rear portion of the housing and opposing projections extend from the rear portion of the housing to limit movement of the container into the housing.

7. The diffusion device of claim 6, wherein the container includes shoulders and the projections abut the shoulders of the container when the container has been sufficiently inserted into the housing.

* * * * *